United States Patent [19]

Schoenwald et al.

[11] Patent Number: 5,382,576
[45] Date of Patent: Jan. 17, 1995

[54] 1-AZA-1-ARYLCYCLOALKANES AS TOPICAL GLAUCOMA TREATMENT AGENTS

[75] Inventors: Ronald D. Schoenwald; Charles F. Barfknecht, both of Iowa City, Iowa

[73] Assignee: University of Iowa Research Foundation, Oakdale, Iowa

[21] Appl. No.: 97,364

[22] Filed: Jul. 26, 1993

[51] Int. Cl.⁶ .................. A61K 31/395; A61K 31/55; A61K 31/54; A61K 31/535
[52] U.S. Cl. .................................... 514/210; 514/212; 514/226.8; 514/227.5; 514/231.2; 514/913
[58] Field of Search ...................... 514/231.2, 210, 255, 514/212, 226.8, 408, 227.5, 913

[56] References Cited

PUBLICATIONS

Bunnett, et al., J. Org. Chem. 1957, 22, 832–4.
Bock, et al., Chemical Abstracts 63:17939b (1965).
Bock, Chemical Abstracts 64:19484h (1966).
Katritzky, et al, J. Org. Chem. 1990, 55, 3205–9.
Embase Abstract 91343346 (1991).
Chemical Abstract 82(25): 171069b (1975).
Journal of Med Chem. 22/11 (1347–1354) 1979 Martin et al.

Primary Examiner—Zohreh Fay
Attorney, Agent, or Firm—Zarley, McKee, Thomte, Voorhees, & Sease

[57] ABSTRACT

Topical treatments for glaucoma using 1-Aza-1-arylcyloalkanes as the treatment agents.

4 Claims, No Drawings

1-AZA-1-ARYLCYCLOALKANES AS TOPICAL GLAUCOMA TREATMENT AGENTS

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive and some surgeons will use surgery only as a last resort.

Carbonic anhydrase inhibitors, prescribed orally, work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults, fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral (through the mouth)—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness comes nausea, tingling in fingers and toes, and other side effects. Oral drugs generally do not, however, cause side effects in the eye.

From the above discussion it can be seen that there is a continuing need for the development of new drugs that can be applied topically in order to avoid systemic affects, and which may at the same time, still be highly effective. This of course necessitates that the compound be one which will, first of all, effectively stimulate a receptor which will provide the correct intraocular pressure, and secondly penetrate the cornea rapidly and distribute well to the active site, i.e. ciliary body of the eye. It goes without saying that compounds which are active as inocular pressure inhibitors, but have limited penetrability across the cornea and into the ciliary body are, as a practical matter, of limited value in developing truly effective topical glaucoma treatments, even though they may have some test activity in vitro, i.e. in a test tube. Put another way, if the compound does not have the correct distribution and penetration properties, its chances of being pharmacologically active when topically applied to an affected eye in patients, are small at best. Thus, it is important, if one is developing effective topical medicaments, that they be active in vitro and that they be active when actually applied to an affected eye from the standpoint of penetrating the cornea and reaching the active site for effective treatment of glaucoma.

Accordingly, it is a primary object of the present invention to provide a new series of compounds, unassociated structurally with those made in the past that have been regarded as likely candidates for topically effective glaucoma treatments with enhanced corneal penetration, ciliary body distribution properties, and which are compounds of quite simplistic chemical structure from the standpoint of their pharmacophore. This latter fact is important in finding the minimum structure necessary to exert a particular pharmacological action, in this case lowering of (intraocular pressure) IOP.

It is another objective of the present invention to prepare new compounds and new treatment methods using those compounds for glaucoma that can be used topically to avoid the undesirable side effects of most systemic treatments.

An even further objective of the present invention is to prepare and use new compounds, differing in structure from those normally regarded as likely candidates for topical actives, which obviously therefore have a new pharmacophore, and therefore open new areas for potential screening for other topically effective candidates.

An even further object of the invention is to prepare a pharmaceutical compositions using these compounds or their biologically active salt forms as effective topical treatments for glaucoma.

The method and manner of accomplishing each of the above objectives, as well as others, will become apparent from the detailed description of the invention which follows hereinafter.

SUMMARY OF THE INVENTION

1-Aza-1-arylcycloalkanes are Used as Effective Topical Glaucoma Treatment Agents. The most preferred compound is 1-phenylpiperidine. This compound represents the simplest structure of the present invention, and thus, may be a new pharmacophore for topical glaucoma treatments.

DETAILED DESCRIPTION OF THE INVENTION

It is not presently known what the precise mechanism of action of the 1-Aza-1-arylcycloalkanes is in effectively treating glaucoma. It is only known that these compounds are topically active. It is possible that they could be carbonic anhydrase inhibitors, but it is also possible that they could work by some other treatment mechanism. Work is currently underway to provide further information on receptor site binding mechanisms, which should reveal the true mechanism of operation. Applicant, however, is not bound by any theory of operation of the present invention, and instead relies upon the simple fact that the compounds do work topically. It is however known from the standpoint of investigating several members of the above identified class that the pharmacophore, i.e the minimum structure necessary to exert the defined intraocular lowering pharmacological effect seems to by 1-phenylpiperidine. 1-phenylpiperidine is a known compound having the following formula:

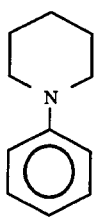

While 1-phenylpiperidine is previously reported in the literature, it has not been recognized as a potential topical glaucoma treatment. The following references discuss the synthesis of this compound, but fail to report any biological activity:

Bunnett, J. F.; Brotherton, T. K. J. Org. Chem. 1957,22,832.

Bock, H.; Kompa, K. L. Angew. Chem. 1965,77,807. Basically, this synthesis of 1-phenylpiperidine as reported in these references comprises the following:

1-Aza-1-arylcycloalkanes [e.g. 1-phenylpiperidine] can be synthesized either by substitution on a preformed heterocycle or by forming the heterocyclic ring from an arylamine. Two reported synthetic routes for 1-phenylpiperidine used the former method. Bunnett & Brotherton refluxed bromobenzene and sodium amide in piperidine. Bock and Kompra heated a combination of benzene, N-chloropiperidine, and aluminum chloride at 80°–100° C. for 1–4 hours.

Substituted compounds (on the piperidine ring and-/or the phenyl ring) can be prepared by the method of Katritzky and Fan where the piperidine ring is formed by reacting glutaraldehyde and primary amines or monosubstituted hydrazines. (Katriktzky, A. R. Fan, W-Q. J. Org. Chem. 1990, 55, 3205-3209]

The 1-aza-1-arylcycloalkanes which can be used to provide effective topical drugs of the present invention have a high degree of penetrability of the cornea so that they can have maximum effective delivery to the active site needed for glaucoma treatment. These compounds have the following generic formula:

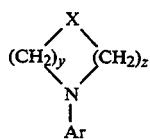

wherein $X=O$, $NH$, $S$, or $CH_2$;
$y=0, 1, 2, 3$; and
$z=1, 2, 3$;

Ar represents phenyl with or without one or more moieties substituted on the 2 through 6 positions. If there are substitutions on the aromatic ring, those substituted moieties may be selected from the group consisting of OH, $OCH_3$, $CH_2OH$, F, Cl, Br, and I. It is preferred that the 1-aza-1-arylcycloalkane ring be a 6-membered cyclo ring, but it is possible that 3, 4 or 5 or even larger than 6-membered cyclo rings may be used. With regard to the aryl ring, it is preferred that it be phenyl, but it may also be a polynuclear aromatic such as naphthyl and other condensed aromatic ring formations. If there are substituents on the ring, it is preferred that those substituents be hydroxy, methoxy, or $CH_2OH$.

Examples of preferred compounds that to date have been made within this general class and tested and demonstrated active are the most preferred compound 1-phenylpiperidine, 1-phenylpiperazine, 1-(3-chlorophenyl)piperazine, 1-(4-chlorophenyl)piperazine, and 4-phenylmorpholine.

As earlier mentioned, most of these compounds are known compounds and therefore one need not dwell on their synthesis. See for example Bunnett and Bock for synthesis techniques for the most preferred compound, 1-phenylpiperidine. Other literature references demonstrate a general synthesis of 1-aza-1-arylcycloalkanes, but generally, those synthesis techniques include the following steps:

1-aza-1-arylcycloalkanes [e.g. 1-phenylpiperidine] can be synthesized either by substitution on a preformed heterocycle or by forming the heterocyclic ring from an arylamine.

As earlier mentioned, compounds falling within the class herein defined, and especially the most preferred compound, 1-phenylpiperidine, have demonstrated in vivo topical effective properties when applied to an affected eye suffering from glaucoma. The key aspects of this invention are the recognition that these compounds are effective topical treatments for glaucoma, the fact that these compounds can be used topically and effectively penetrate the cornea and move to the active site, and the fact that they are simple in structure and appear to cause no eye irritation, while being active at physiological pH.

Since all of the compounds of the present invention are substituted amines, i.e. nitrogen with all three positions filled, they will form hydrochloride salt forms which are known to be active. It is understood that the compounds referred to herein cover the compounds themselves and their biologically active salt forms.

Typically, the method of administration is simply preparing a water soluble salt (e.g. hydrochloride) with a suitable pharmaceutical carrier and topically administering the solution. The amount of active use in the composition should be from about 0.25% by weight to about 5% by weight for an eye drop composition, preferably from about 0.5% by weight to about 2.0% by weight. The important point is not the dose amount, but simply that it be an amount that is effective in treating glaucoma and yet not be so strong as to provide eye irritation or side effects. Generally amounts within the ranges herein specified are satisfactory.

The diluent for the eye drop composition may be an isotonic eye treatment carrier buffered to a pH of from about 4 to about 8 and typically it will contain small amounts of conventional wetting agents and anti-bacterial agents. The preferred pH is within the range from about 6.8 to about 7.8 and contain sufficient sodium chloride or equivalent to be isotonic. Anti-bacterial agents where they are included may be within the range of from about 0.004% (W/V) to about 0.02% (W/V) of the composition.

EXAMPLES

The following examples of certain compounds of the present invention obtained in accordance with conventional synthesis procedures earlier described and in some instances obtained commercially were tested for their topical effect in lowering IOP. IOP was measured using a pneumatonograph (Digilabs Model 30D, Cambridge, Mass.) and 1-2 drops of 0.5% proparacaine hydrochloride used topically for anesthesia. IOP is measured in both eyes. The active drug (2%) is dissolved in a pH 7.4 phosphate buffer and instilled (50 L) into the lower conjunctival sac of the right eye only.

The "IOP recovery rate assay" as reported by Vareilles and Lotti (Ophthal. Res., 13, 72–79, 1981) was used. In this assay 20% sodium chloride solution was infused into the marginal ear vein of New Zealand White rabbits for 10 minutes at a rate of 1 mL/min (N=12). IOP was measured at 15, 25, 35, 45, 60, 75, 90 and 120 minutes with an applanation pneumatonometer (Digilab Model D). Fifty L of a 2% solution or suspension of derivatives of 1-aza-1-arylcycloalkanes containing a pH 7.4 phosphate buffer was administered topically to the right eye 60 minutes before the start of the sodium chloride infusion. Control animals were given vehicle without drug.

The hypertonic sodium chloride solution causes a temporary decline in IOP which returns to normal IOP in about 90 minutes if no drug is administered. IOP gradually returns to normal at a constant rate but more slowly if the in vivo secretion rate of aqueous humor is reduced due to the presence of drug. The return to normal IOP is measured from the positive linear slope which is a measure of the constant rate of return to normal IOP and begins at about 30–45 minutes after starting the NaCl infusion. A comparison of the slope with and without the addition of test agent to the rabbit eye is expressed as "% decrease in slope".

The results for the test compounds:
1-(3-chlorophenyl)piperazine HCl
1-phenylpiperazine HCl
1-phenylpiperidine HCl
4-phenylmorpholine HCl
1-(4-chlorophenyl)piperazine HCl
are reported in Table 1 below.

TABLE 1

| TEST COMPOUND | Avg. Drug Treated Rabbits (slope) | Avg. Blank Treated Rabbits (slope) | % Decrease in Slope |
|---|---|---|---|
| 1-(3-chlorophenyl) piperazine HCl | 0.0573 ± 0.0214 | 0.0636 ± 0.0321 | 9.89 |
| 1-phenylpiperazine HCl | 0.0500 ± 0.0197 | 0.0660 ± 0.0318 | 24.2 |
| 1-phenylpiperidine HCl | 0.0634 ± 0.0111 | 0.0840 ± 0.0183 | 24.6 |
| 4-phenylmorpholine HCl | 0.0790 ± 0.0343 | 0.1023 ± 0.0366 | 22.8 |
| 1-(4-chlorophenyl) piperazine HCl | 0.0593 ± 0.0189 | 0.0744 ± 0.0226 | 17.3 |

The hypertonic sodium chloride causes a decline in IOP which then recovers at a rate dependent on the activity of carbonic anhydrase. IOP gradually returns to normal at a constant rate but much more slowly if a carbonic anhydrase inhibitor is present in the eye in sufficient concentration. The return to normal is measured from the positive linear slope which begins at about 30–45 minutes after starting the infusion.

If the drug is active the topically treated rabbit eyes show a slower recovery to initial IOP values. The recovery rate is appropriately linear and a slope is measured for the control and treated rabbit eyes. The results are expressed in the table as a percent decrease in slope for the treated eyes compared to the control eyes along with the probability. In the same test, topically applied buspirone (2%) showed no change in slope. Although it is a piperazine structure, buspirone is devoid of activity. Also, in the present model, timolol, Murck) lowered IOP by about 40% (Vareilles and Lotti (Ophthal. Res., 13, 72–79, 1981). It therefore can be seen that the compounds of the present invention are nearly as active as the standard topical (timolol eye drops) and more active than a similar chemical structure, buspirone. These data demonstrate good topical activity. The most effective compound is the pharmacophore, 1-phenylpiperidine.

The following claims are intended to define the invention with the understanding that certain changes may be made in the structures therein exposed and still come within the spirit and scope of the invention. For these changes, applicant relies upon the proper application of the doctrine of equivalence to provide the coverage equitably allowed for this invention.

What is claimed is:

1. A method of reducing intraocular eye pressure, said method comprising:
topically applying to an affected eye a small but therapeutically effective intraocular eye pressure reducing amount of compound of the formula:

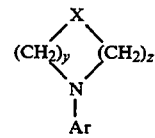

wherein:
X is oxygen, sulphur or methylene;
Y is 0, 1, 2 or 3;
Z is 1, 2, or 3; and
Ar is a phenyl moiety.

2. The method of claim 1 wherein the compound is 1-phenylpiperidine.

3. The method of claim 1 wherein the active compound is dosed from an eye drop composition containing from about 0.25% by weight to about 5% by weight of active in the eye drop composition.

4. The method of claim 1 wherein the dose amount is from about 0.5% by weight to about 2% by weight of said composition.